United States Patent [19]
Evans, Sr.

[11] Patent Number: 5,029,576
[45] Date of Patent: Jul. 9, 1991

[54] METHOD AND APPARATUS FOR CLEANING TEETH AND GUMS

[76] Inventor: Don A. Evans, Sr., 404 Business Center Dr., Birmingham, Ala. 35244

[21] Appl. No.: 205,654

[22] Filed: Jun. 13, 1988

[51] Int. Cl.⁵ .............................................. A61H 9/00
[52] U.S. Cl. ........................................ 128/66; 433/80
[58] Field of Search ................ 128/62 A, 66; 433/80, 433/215, 216; 210/695

[56] References Cited

U.S. PATENT DOCUMENTS

| | | | |
|---|---|---|---|
| 2,939,830 | 6/1960 | Green et al. | 210/695 X |
| 3,228,878 | 1/1966 | Moody | 210/695 |
| 3,380,446 | 4/1968 | Martin | 128/24 |
| 3,514,328 | 9/1970 | Malin | 134/1 |
| 4,012,842 | 3/1977 | Vit | 32/58 |
| 4,265,746 | 5/1981 | Zimmerman, Sr. et al. | 210/695 |
| 4,265,754 | 5/1981 | Menold | 210/695 X |
| 4,407,719 | 10/1983 | Van Gorp | 210/695 |
| 4,422,450 | 12/1983 | Rusteberg | 128/66 X |
| 4,501,661 | 2/1985 | Karasawa | 210/695 X |
| 4,502,497 | 3/1985 | Siahou | 433/216 X |
| 4,552,664 | 11/1985 | Benner | 210/695 |
| 4,564,448 | 1/1986 | O'Meara, Jr. | 210/695 X |
| 4,595,365 | 6/1986 | Edel et al. | 433/216 |
| 4,605,498 | 8/1986 | Kulish | 210/695 X |
| 4,659,479 | 4/1987 | Stickler et al. | 210/695 |
| 4,682,584 | 7/1987 | Pose | 433/215 X |
| 4,734,202 | 3/1988 | Mach | 210/695 |

FOREIGN PATENT DOCUMENTS

| | | | |
|---|---|---|---|
| 3433417 | 3/1986 | Fed. Rep. of Germany | 210/695 |
| 2132588 | 6/1987 | Japan | 210/695 |
| 8705003 | 8/1987 | World Int. Prop. O. | 210/695 |

OTHER PUBLICATIONS

Grutsch, J. F., and McClintock, W. J., "Corrosion and Deposit Control in Alkaline Cooling Water Using Magnetic Water Treatment at Amoco's Largest Refinery", *Corrosion 84*, Paper Number 330 (1984).

Primary Examiner—Robert P. Swiatek
Assistant Examiner—Nicholas D. Lucchesi
Attorney, Agent, or Firm—Wm. Randall May

[57] ABSTRACT

A method and apparatus for cleaning and treating teeth and gums, for the removal of plaque and calculus build-up on teeth, and for the prevention of plaque and calculus formation on teeth thus reducing or eliminating susceptibility of dental and gum related diseases. The method comprises the passing of fluid particles through a magnetic field of a predetermined minimum strength wherein the fluid particles are caused to flow through the magnetic field in a south pole to north pole direction. The magnetically treated fluid is then applied to the teeth and gums. A preferred embodiment comprises a conventional, pulsating, high velocity fluid stream, tooth and gum cleaning machine for delivery of the magnetically treated fluid to the surface of the teeth and gums.

2 Claims, 4 Drawing Sheets

METHOD AND APPARATUS FOR CLEANING TEETH AND GUMS

BACKGROUND OF THE INVENTION

I. Field of the Invention

The present invention relates to a new method and apparatus for cleaning and treating teeth and gums, and in particular, to a new method and apparatus of interrupting and arresting the natural formation of plaque and calculus on teeth.

II. Prior Art and Other Considerations

In 1832 Professor Joseph Faraday demonstrated that if a fluid is passed across the lines of force of a magnetic field, an electrical current is produced. In 1879 Professor E. H. Hall discovered that when a fluid is passed across the lines of force of a magnetic field, thereby producing the Faraday Current, a drift force is also created which tends to separate the charged particles which occur naturally in the fluid due to the process known as ionization.

Ionization is the natural process of the exchange, gain or loss, of electrons between atoms or molecules. It is this process which accounts for the formation and build-up of plaque and calculus deposits on teeth.

The use of magnetic fields to treat various properties of fluids, particularly water, is well-known within the realm of industrial and/or commercial activity. Typically, such treatment has been used in the prevention of scale build-up or to prevent the formation of encrustations on surfaces generally associated with the various aqueous environments inherent to such industrial or commercial activities. Devices for propelling pulsating jet streams of fluid against the surfaces of teeth and gums for the purpose of oral hygiene are well-known in the prior art.

The problem of "mineral scaling" in the mouth is caused by the secretion of naturally occurring minerals through the saliva glands. These minerals mix with the bacteria plaque line. If not removed within approximately 24 hours, the formation will harden into what is commonly called calculus. The build-up occurs much as a coral reef is formed and works below the gum line. Bacteria utilizes this area of calculus build-up as a breeding ground from which bone and soft tissue are attacked.

Dental diseases are caused by microbial infections involving identified microbial populations. These populations utilize colonization as a pathogenic modality and colonization is thought to be dependent upon plaque formation. Accordingly, by the prevention of plaque and calculus formation on teeth, dental diseases could also be prevented.

There exists, therefore, a need for a method and device which will stop and reverse the formation of plaque and calculus on teeth, however, due to the presence of electrovalent bonding, the removal of plaque and calculus, once formed, from the surfaces of teeth presents a very difficult task. At the present time, devices or method for the "effective" removal of plaque and calculus from the surface of teeth are limited to either the metal tools and procedures used by dentists or dental personnel to scrape away such build-up or to the use of ultra sonic techniques. While both techniques have generally proven to be effective in removing plaque and calculus from the surfaces of teeth, neither technique is available to the general public without professional supervision and/or assistance and the associated expense.

SUMMARY OF THE INVENTION

The present invention relates to a method and apparatus which reverses and prevents the build-up of plaque and calculus on teeth. More particularly, the invention inhibits the ionization in a fluid by passing the fluid through a magnetic field having certain parameters, the magnetically treated fluid is then applied to the surfaces of the teeth and gums.

It has been determined through investigation and experiment, that effective ionization reduction in a fluid can be accomplished by passing the fluid through a magnetic field having a field strength of an Alnico-V bar or rod magnet or by the use of an electromagnet or other magnetic field producing device which produces an equivalent field strength and similar field envelope. It has also been found that in order to achieve ionization reduction, in all cases the fluid must flow first through the magnetic force field produced by the south pole of the magnet and then through the magnetic force field produced by the north pole of the magnet.

By passing the fluid through this controlled strength magnetic field in such a manner, an abundance of free electrons is produced. The presence of the free electrons cancels or nullifies the by-products of ionization by preventing the electrovalent bond that would normally occur between the molecules of the fluid.

By applying such magnetically treated fluid to the surfaces of the teeth and gums, the natural process of electrovalent bonding, and thus the formation of plaque and calculus, is interrupted and virtually stopped.

An apparatus which maintains the above-mentioned parameters is provided. An elongated bar or rod magnet is housed within the apparatus housing so as to be directionally oriented and parallel and as close as possible to the fluid conduit. This is accomplished, in a preferred embodiment, by attaching or securing the magnet directly to the exterior surface of the fluid carrying conduit and by placing the magnet parallel to the conduit with the south pole of the magnet positioned on the fluid entrance side of the conduit and the north pole on the fluid exit side. The treated fluid thus produced is then propelled against the surfaces of the teeth and gums.

The method and apparatus of the present invention provides the necessary parameters for optimum reduction of ionization within the fluid and the resulting production of free electrons necessary to break down the electrovalent bonding of plaque and calculus on teeth. The apparatus accomplishes this in a safe, simple, inexpensive manner which can be used by the general public without the need for professional supervision or assistance.

An object of the invention is to provide a new teeth and gum cleaning method and apparatus.

An advantage of the invention is to provide a magnetic treatment method and apparatus which interrupts the natural process of plaque and calculus formation on teeth.

Another advantage of the invention is to provide a magnetic treatment method and apparatus which removes and controls plaque and calculus build-up on the surfaces of teeth above and below the gum lines.

Yet another advantage of the invention is to provide a safe, inexpensive, method and means for the effective removal of plaque and calculus from the surfaces of teeth for use by the public in general without the need for professional supervision or assistance.

An additional advantage of the present invention is to provide a teeth and gum cleaning method and apparatus which can be effective in the prevention and control of dental and gum related diseases.

BRIEF DESCRIPTION OF THE DRAWINGS

The foregoing and other objects, features, and advantages of the invention will be apparent from the following more particular description of preferred embodiments as illustrated in the accompanying drawings in which reference characters refer to the same parts throughout the various views. The drawings are not necessarily to scale, emphasis instead being placed upon illustrating the principles of the invention.

DETAILED DESCRIPTION OF THE DRAWINGS

Figure 1:
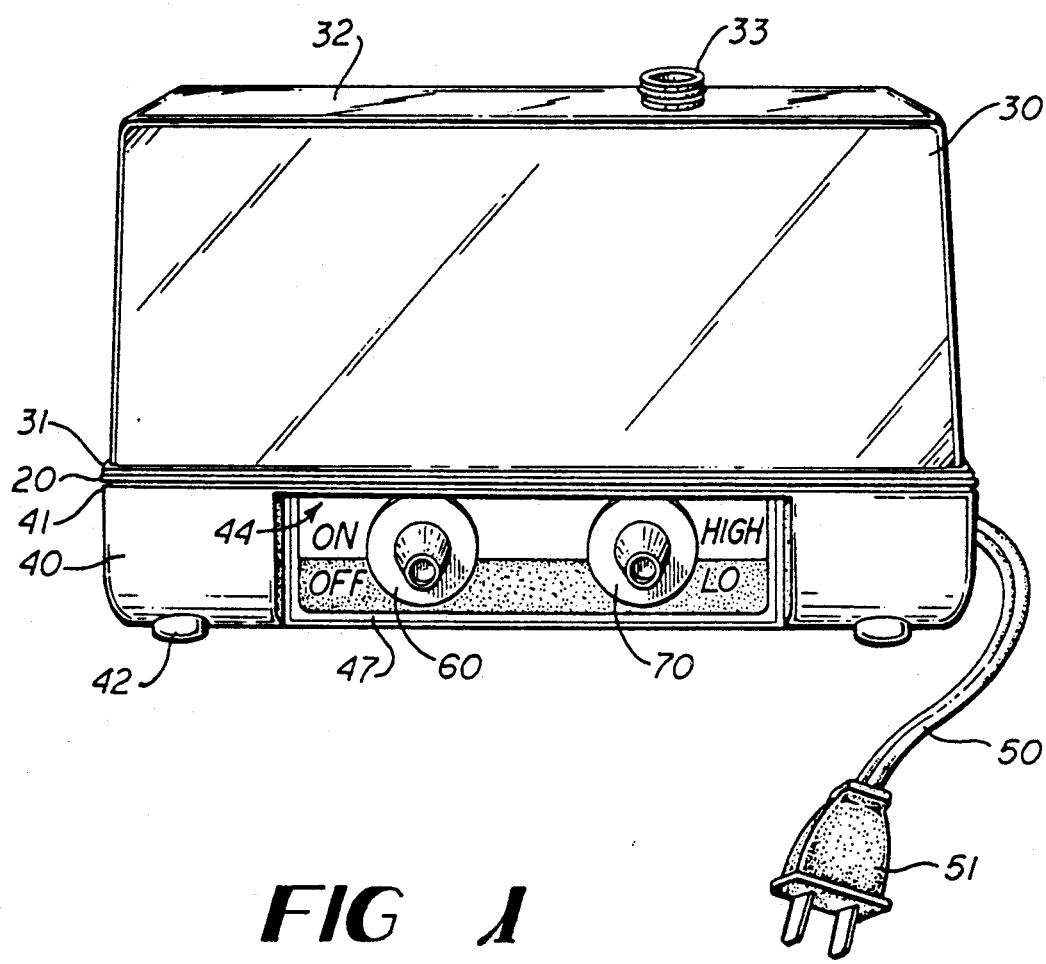
FIG. 1 is a front view of a system for cleaning and treating teeth and gums according to an embodiment of the invention with a top cover of the system in place as designed for periods of none use.
Figure 2:
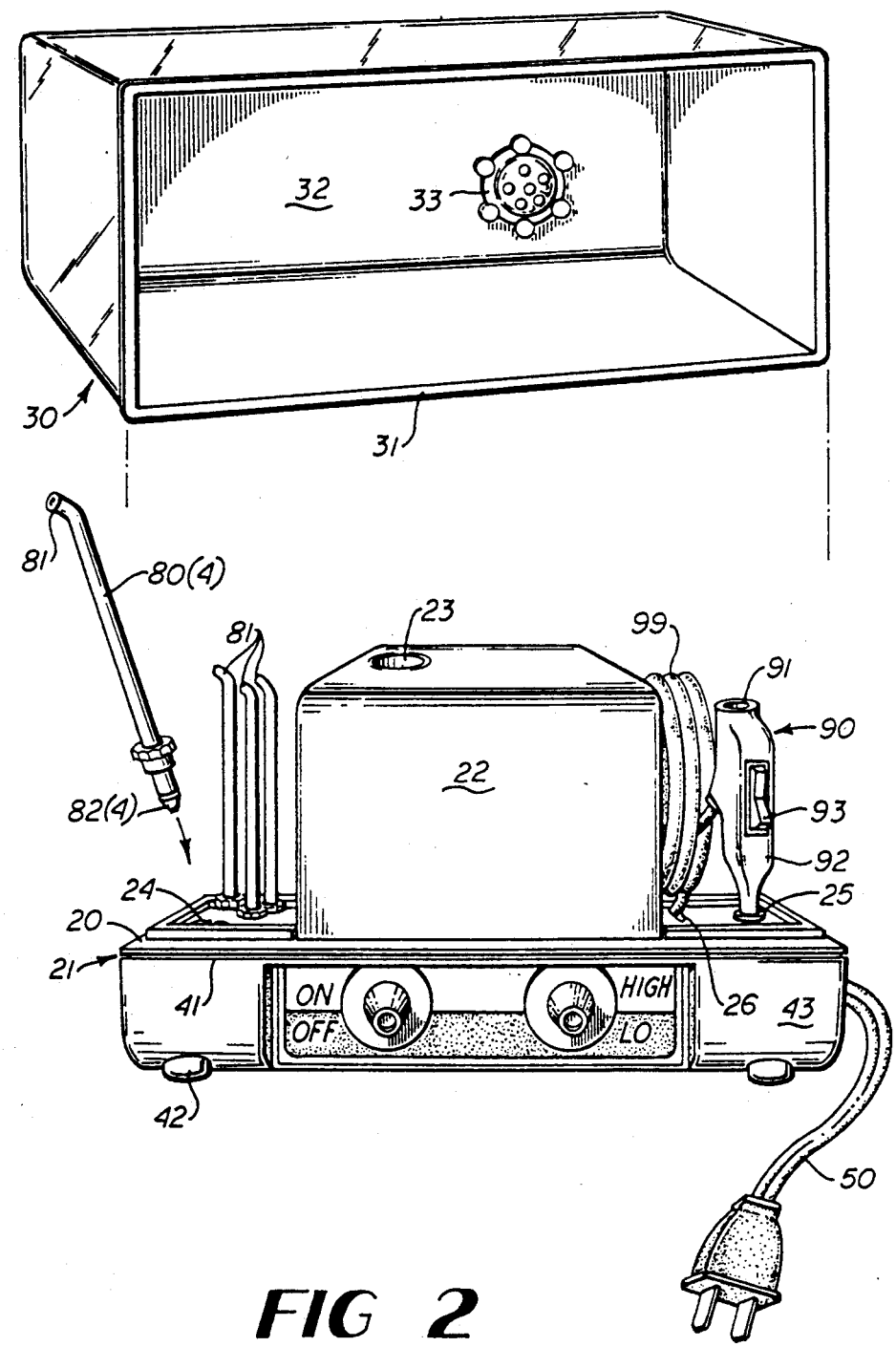
FIG. 2 is a front view of the system of FIG. 1 with the top cover removed as well as a view of the top cover lying on its side and viewed from the bottom.
Figure 3:
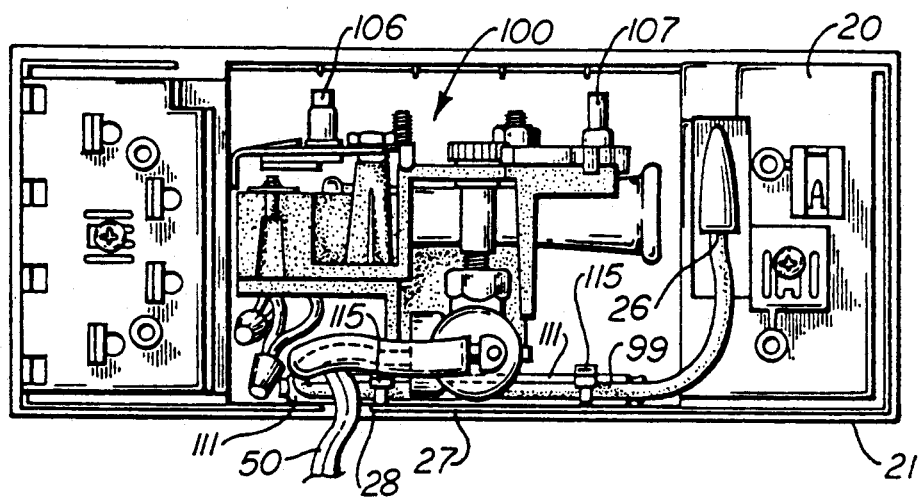
FIG. 3 is a bottom view of the system of FIG. 2 with a bottom cover removed.
Figure 5:
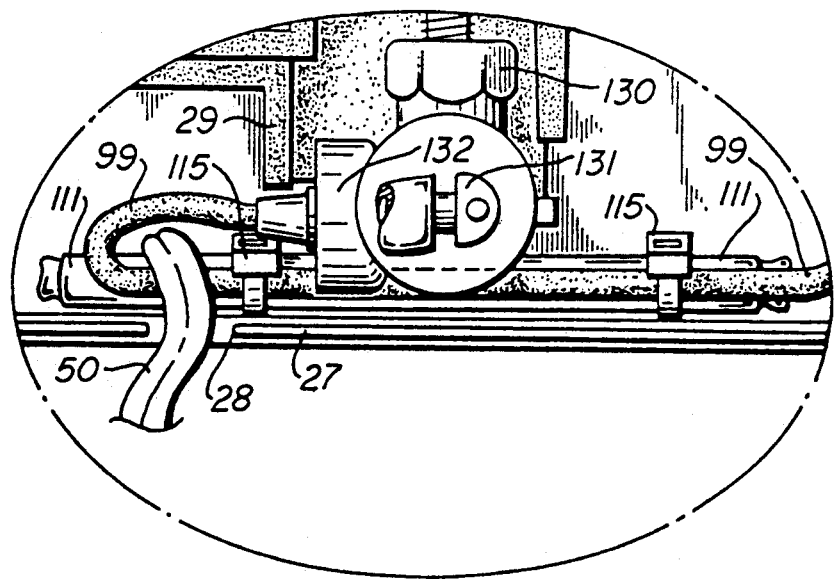
FIG. 5 is an enlarged view of the encircled apparatus of FIG. 4.
Figure 4:
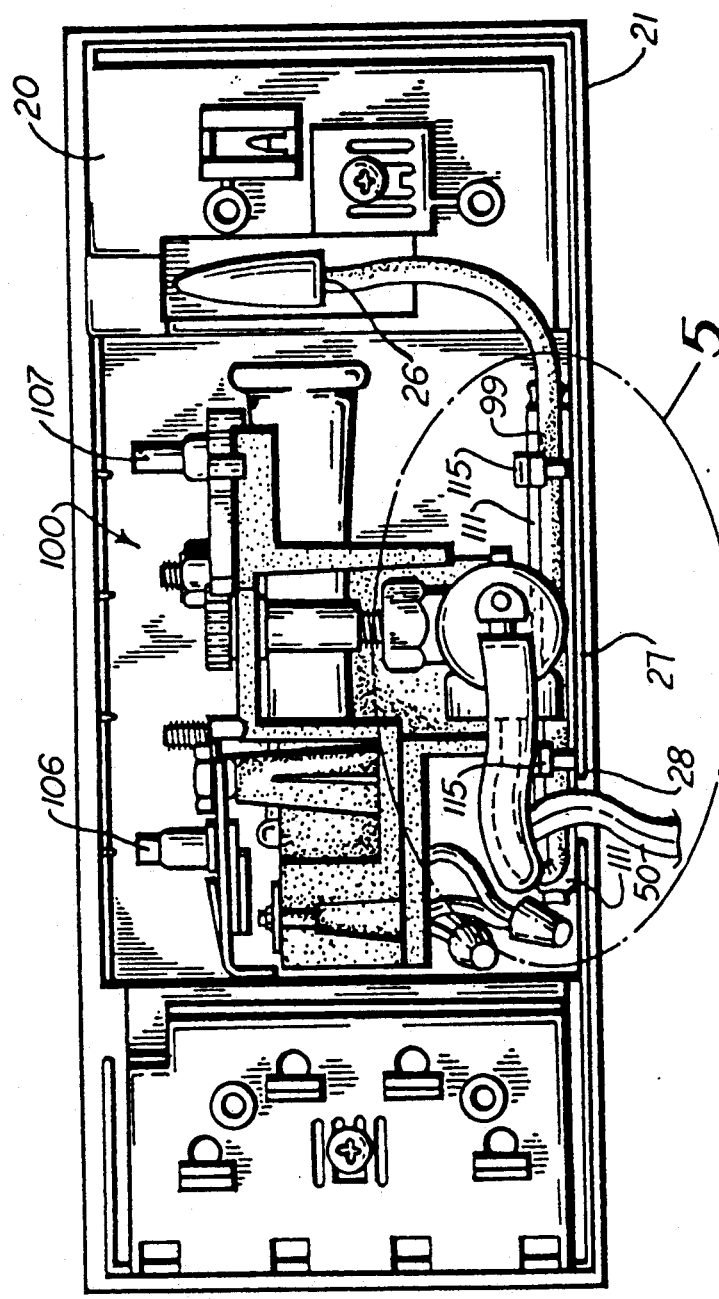
FIG. 4 is a slightly enlarged view of the system of FIG. 3 with the location of the apparatus of the embodiment of the invention encircled.

A system for cleaning and treating teeth and gums of FIG. 1, FIG. 2, FIG. 3, and FIG. 4 is typical of those employing techniques of applying to the teeth and gums, water in the form of a pulsating, high velocity stream. This system consists of a chassis 20, a top cover 30, a bottom cover 40, a power cord 50, a power switch knob 60, a pulse rate control knob 70, a set of nozzles 80, an applicator handle/controller assembly 90, and an internal mechanism 100.

The internal mechanism 100 is securely attached to the chassis 20. The bottom cover 40 is securely attached to the chassis 20. Just above a top edge 41 of the bottom cover 40, the chassis is formed into a groove 21. The chassis 20 is shaped to form a cap 22 which shrouds the internal mechanism 100. At the top of the cap 22, there is a funnel neck port 23. To the left of the cap 22, the chassis 20 is formed to have four (4) nozzle receptacles 24. To the right of the cap 22, the chassis 20 is formed to have an applicator assembly receptacle 25. Near the applicator assembly receptacle 25, there is an outlet tube port 26. Along the rear side 27 of the chassis cap 22 just below the level of the groove 21, there is a mating surface notch 28. The chassis 20, inside the cap 22, has a structural mounting protrusion 29.

The top cover 30 is generally in the shape of a rectangular box with an open bottom. In the top surface 32, there is a top cover funnel assembly 33 positioned so that when the top cover 30 is turned upside down and aligned with the cap 22 of the chassis 20, said top cover funnel assembly 33, when aligned with, fits inside the funnel neck port 23. The bottom edge 31 has a shape that is complementary to the groove 21 of the chassis 20.

The bottom cover 40 is generally in the shape of a rectangular box with an open top. On the exterior, near each corner of the bottom surface is a leg 42. The front exterior surface 43 has a recess 44. Near the center vertically, and somewhat to the left of center horizontally, of the recess 44 is a left hole 45. Near the center vertically, and somewhat to the right of center horizontally, of the recess 44 is a right hole 46. Applied to the exterior surface of the recess 44 is a label 47. Along the top edge 41 of the rear face of the bottom cover 40 is a notch 48 at a point in alignment with the mating surface notch 28.

The power cord 50 has a standard plug 51 and passes through the bottom cover notch 48. It is connected, as required, to the internal mechanism 100.

The power switch knob 60 securely slides onto a power switch shaft 106.

The pulse rate control knob 70 securely slides onto a pulse rate control shaft 107.

Each nozzle 80 has an input end 81 and an exit end 82. The output end 82 of each nozzle 80 is curved to facilitate the application of the cleaning fluid.

The applicator handle/controller assembly 90 consists of a handle/controller 92 and an outlet tube 99. The handle/controller 92 has a fluid flow cut-off switch 93 near the middle of the handle/controller 92. At the end of the handle/controller 92 opposite the end connecting to the outlet tube 99 is a nozzle retainer 91.

The internal mechanism 100 consists of a path for the flow, treatment and processing of water, as well as various devices providing for said processing and the control of said processing; an additional part of the internal mechanism 100 is a Alnico-V type bar magnet 111. This path includes a pump inlet tube 120 and a pump 130. The pump 130 has an inlet port 131 and an outlet port 132. The exit of the inlet tube 120 is attached to the inlet port 131 of the pump 130; this connection is leakproof. The outlet port 132 of the pump 130 is attached to the inlet end of the outlet tube 99; this connection is leakproof. The bar magnet 111 is mounted immediately adjacent to and parallel with the outlet tube 99 in the vicinity of the pump 130 inside the cap 22 using mounting bands 115. It is mounted so that a path along the outlet tube 99 from the end of the bar magnet 111 designated as the south pole to the outlet port 132 is shorter than a path along the outlet tube 99 from the end of the bar magnet 111 designated as the north pole to the outlet port 132. A south pole end of the magnet 111 is separated from a north pole end of the magnet 111 by a distance which is on the order of the length of the outlet tube 99.

The outlet tube 99 is connected from the exit port 132 of the pump 130 to the handle/controller 92.

In preparation for operation, after plug 51 is inserted into a convenient electrical outlet, the top cover 30 is removed. The applicator handle/controller assembly 90 is removed from the applicator assembly receptacle 25 in the chassis 20; one of the nozzles 80 is removed from the nozzle receptacle 24. The input end 81 of the nozzle 80 is inserted into the nozzle retainer 91 of the applicator handle/controller assembly 90. The top cover 30 is inverted and placed on top of the chassis cap 22 so that the top cover funnel assembly 33 is aligned with, and fits inside, the funnel neck port 23.

The top cover is filled with tap water, the power is turned on using the power switch knob 60. The pulse rate is set to a desirable level using the pulse rate control knob 70.

The output end 82 of nozzle 80 is aimed at the desired area of the teeth and/or gums and the fluid flow cut-off switch 93 is slid in the direction of the nozzle allowing the water flow to begin.

In operation, the water flows from the inverted top cover 30 through the top cover funnel assembly 33 and the funnel neck port 23 into the internal mechanism 100.

The internal mechanism 100 is a unit which receives water from the inverted top cover 30 and power from the power cord 50 and delivers magnetically treated water in a pulsating, high velocity stream through the outlet tube 99.

The path of the water through the internal mechanism 100 begins at the funnel neck port 23 and continues through the inlet tube 120 to the inlet port 131 of the pump 130. The water exits the pump 130 through the outlet port 132 and exits the internal mechanism 100 through the outlet tube 99.

Advantageously, water passing through the outlet tube passes through the magnetic field emanating from bar magnet 111.

The magnetically treated water continues its journey through the outlet tube 99 through the applicator handle/controller assembly 90 and through the nozzle 80 whereupon it is delivered to the surfaces of the teeth and/or gums.

Water so magnetically treated and applied to the teeth and gums not only removes plaque and calculus build-up but also prevents such formation thereby reducing or eliminating susceptibility to dental and gum related diseases.

While the invention has been particularly shown and described with reference to the preferred embodiments thereof, it will be understood by those skilled in the art that various alterations in form and detail may be made therein without departing from the spirit and scope on the invention.

What is claimed is:

1. An apparatus for cleaning and treating teeth and gums and for the interruption, reversal and prevention of the formation of plaque and calculus on teeth comprising:

a chassis;

an applicator handle;

pump means connected by an inlet tube to a source of fluid and by an outlet tube to said applicator handle; said pump means serving to supply a high velocity stream of fluid through said outlet tube and to said applicator handle; said pump means, said inlet tube, and said outlet tube being situated internally in said chassis; at least a portion of said applicator handle being external to said chassis and having a nozzle to facilitate the application of said high velocity stream of fluid to the teeth and gums; and, an elongated magnet mounted proximate and parallel to a path travelled by said fluid through said outlet tube for creating a magnetic field at least on the order of that produced by an Alnico-V magnet; said magnetic field being oriented so that said fluid in said outlet tube is passed first through the magnetic force field produced by the south pole of said magnetic field produced by said elongated magnet and then through the magnetic force field produced by the north pole of said magnetic field produced by said elongated magnet.

2. The apparatus of claim 1, wherein a south pole end of said magnet is separated from a north pole end of said magnet by a distance which is on the order of the length of said outlet tube.

* * * * *